(12) United States Patent
Gold et al.

(10) Patent No.: US 8,330,133 B2
(45) Date of Patent: Dec. 11, 2012

(54) SUPPORT FRAME FOR RADIATION SHIELD GARMENT AND METHODS OF USE THEREOF

(76) Inventors: Deborah L. Gold, Long Beach, CA (US); Steve Forman, Manhattan Beach, CA (US); Danny Gennawey, Yorba Linda, CA (US)

( * ) Notice: Subject to any disclaimer, the term of this patent is extended or adjusted under 35 U.S.C. 154(b) by 296 days.

(21) Appl. No.: 12/871,591

(22) Filed: Aug. 30, 2010

(65) Prior Publication Data

US 2012/0047639 A1 Mar. 1, 2012

(51) Int. Cl.
*G21F 3/02* (2006.01)

(52) U.S. Cl. .............. 250/516.1; 250/505.1; 250/515.1; 250/519.1; 2/2.12; 2/455; 2/456; 2/457; 2/460

(58) Field of Classification Search .............. 2/457, 455, 2/456, 2.12, 459, 460, 492; 250/505.1, 515.1, 250/516.1, 519.1

See application file for complete search history.

(56) References Cited

U.S. PATENT DOCUMENTS

| 4,286,601 | A | | 9/1981 | Farino |
| 5,028,796 | A | | 7/1991 | Swartz |
| 5,183,194 | A | * | 2/1993 | Shirdavani .................... 224/634 |
| 5,745,925 | A | | 5/1998 | Ghilardi et al. |
| 5,844,246 | A | * | 12/1998 | Marchione ................. 250/516.1 |
| 2007/0074327 | A1 | * | 4/2007 | Davies et al. ........................ 2/44 |
| 2009/0114857 | A1 | * | 5/2009 | DeMeo et al. ............. 250/516.1 |
| 2011/0253914 | A1 | * | 10/2011 | Rees ......................... 250/516.1 |

* cited by examiner

*Primary Examiner* — David A Vanore
*Assistant Examiner* — Nicole Ippolito
(74) *Attorney, Agent, or Firm* — Heidi L. Eisenhut; Loza & Loza, LLP

(57) ABSTRACT

Embodiments of the invention are directed to a support frame for alleviating the weight and stress inflicted upon the shoulders and neck of individual caused by wearing a radiation shield garment and methods of use thereof. In one embodiment, the support frame comprises an elongated upper vertical back members slidably coupled to a lower vertical back member to provide vertical height adjustment; a lower back support panel coupled to the lower vertical back member to provide lower back support to the wearer; and a pair of shoulder members attached to the upper top end of the elongated vertical back member to support shoulder regions of the radiation shield garment.

18 Claims, 5 Drawing Sheets

SUPPORT FRAME FOR RADIATION SHIELD GARMENT AND METHODS OF USE THEREOF

FIELD OF INVENTION

At least one feature pertains to a support frame for a radiation shield garment and methods of use thereof.

BACKGROUND OF INVENTION

It is well-known to provide protective garments to personnel working in or near a radioactive environment, to health care workers operating x-ray equipment or working in radiology laboratories. Generally, such radiation shield garments are extremely heavy because they include one or more layers of lead sheet material to provide the desired protection. Extended use of such garments may become burdensome and tiring to the wearer with extended use. This is particularly true when the weight of the garment is borne primarily and/or unremittingly by the wearer's shoulders and neck. For example, persons exposed to x-rays typically wear aprons and/or other apparel made from material having a large lead and/or other heavy metal content, designed to absorb harmful radiation to which the user might otherwise be exposed. Such aprons may weigh in the range of about 8 to about 25 pounds. Since users (or wearers), such as x-ray technicians, radiologists, etc. frequently have to wear them for extended periods of time, they often become tiring and even painful, particularly when the sole or primary support is substantially or constantly one portion of the wearer's body. The shoulders, because of their physiological structure and their relatively high position on the body as a whole, are particularly susceptible to these effects.

Consequently, a support frame to be worn by the wearer which alleviates the problems inherent in extended use of protective radiation shield garments as described previously is needed.

SUMMARY OF INVENTION

A support frame for a radiation shield garment, comprising: (a) an elongated upper vertical back member, having an upper top end and an upper bottom end; (b) a lower vertical back member, having a lower top end and a lower bottom end, the lower top end of the lower vertical back member slideably attached to the upper bottom end of the elongated upper vertical back member; (c) a lower back support panel coupled to the lower bottom end of the lower vertical back member; and (d) a pair of shoulder members attached to the upper top end of the elongated vertical back member is herein disclosed.

Each shoulder member may comprise: (i) base; and (ii) a shoulder bracket projecting upwardly in a curved manner from the base for extending over shoulders of a wearer. The base may include one or more slots providing angular adjustment of the pair of shoulder members and wherein one or more fasteners extend through the one or more slots slideably attaching the each shoulder member to the upper top end of the elongated upper vertical back member. The support frame may further comprise one or more inwardly facing upper padded members coupled to the base of the each of the pair of shoulder members and positioned to rest upon a shoulder area of the wearer.

The upper bottom end of the elongated upper vertical back member may include one or more longitudinal slots; and wherein one or more fastening means extend through the elongated slots providing vertical height adjustment of the elongated upper vertical back member. The lower back support member may be positioned to rest upon a lower back area of a wearer. The support frame may further comprise a strap integrally connected to the lower back support member. The strap may comprise a first end and a second end, the second end comprising an attaching means integral thereto. The support frame may further comprise an inwardly facing center padded member attached to the upper bottom end of the lower vertical back member and positioned to rest upon a lower back area of a wearer. The upper top end of the elongated upper vertical back member may have a V-shaped configuration and the lower bottom end of the lower vertical back member has an upside down T-shaped configuration. The elongated upper vertical back member, the lower vertical back member, and the pair of shoulder members attached to the upper top end of the elongated vertical back member may be comprised of a material selected from the group consisting of aluminum and polypropylene.

A support frame for a radiation shield garment, comprising: (a) an elongated upper vertical back member, having an upper top end and an upper bottom end, the upper top end branching into a left portion and a right portion; (b) a lower vertical back member, having a lower top end and a lower bottom end, the lower top end of the lower vertical back member slideably attached to the upper bottom end of the elongated upper vertical back member; (c) a lower back support member attached to the lower bottom end of the lower vertical back member; and (d) a pair of shoulder members attached to the upper top end of the elongated vertical back member, each of the pair of should members comprising: (i) a base; and (ii) a rigid attachment strap projecting upwardly in a curved manner from the base for extending over shoulders of a wearer is herein disclosed.

The base may include one or more slots providing angular adjustment of the pair of shoulder members and wherein one or more fasteners extend through the one or more slots slideably attaching the each shoulder member to the upper top end of the elongated upper vertical back member. The upper bottom end of the elongated vertical back member may include one or more longitudinal slots; and wherein one or more fastening means extend through the elongated slots providing vertical height adjustment of the elongated upper vertical back member. The support frame may further comprise a strap integrally connected to the lower back lower padded member. The strap may comprise a first end and a second end, the second end comprising an attaching means integral thereto. The support frame may further comprise an inwardly facing center padded member attached the upper bottom end of the lower vertical back member and positioned to rest upon a lower back area of the wearer. The upper top end of the elongated upper vertical back member may have a V-shaped configuration and the lower bottom end of the lower vertical back member has an upside down T-shaped configuration. The elongated upper vertical back member, the lower vertical back member, and the pair of shoulder members may be attached to the upper top end of the elongated vertical back member are comprised of aluminum.

A support frame for a radiation shield garment, comprising: (a) an elongated upper vertical back member, having an upper top end and an upper bottom end; (b) a lower vertical back member, having a lower top end and a lower bottom end, the lower top end of the lower vertical back member slideably coupled to the upper bottom end of the elongated upper vertical back member; (c) a lower back support member attached to the lower bottom end of the lower vertical back member; (d) an inwardly facing center padded member attached to the upper bottom end of the lower vertical back member and positioned to rest upon the lower back of the wearer; (e) a pair of shoulder members attached to the upper top end of the elongated vertical back member, each of the pair of should members comprising: (i) a base; (ii) a shoulder bracket projecting upwardly in a curved manner from the base for extending over shoulders of a wearer; and (iii) an inwardly facing upper padded member coupled to the base the each of the pair of shoulder members and positioned to rest upon a shoulder area of the wearer is herein disclosed.

BRIEF DESCRIPTION OF THE DRAWINGS

The features, nature, and advantages of the present aspects may become more apparent from the detailed description set forth below when taken in conjunction with the drawings in which like reference characters identify correspondingly throughout.

DETAILED DESCRIPTION

The following detailed description is of the best currently contemplated modes of carrying out the invention. The description is not to be taken in a limiting sense, but is made merely for the purpose of illustrating the general principles of the invention.

Embodiments of the invention are directed to a support frame for alleviating the weight and stress inflicted upon the shoulders and neck of individual caused by wearing a radiation shield garment and methods of use thereof. In one embodiment, the support frame comprises an elongated upper vertical back members slidably coupled to a lower vertical back member to provide vertical height adjustment; a lower back support panel coupled to the lower vertical back member to provide lower back support to the wearer; and a pair of shoulder members attached to the upper top end of the elongated vertical back member to support shoulder regions of the radiation shield garment.

Figure 1:
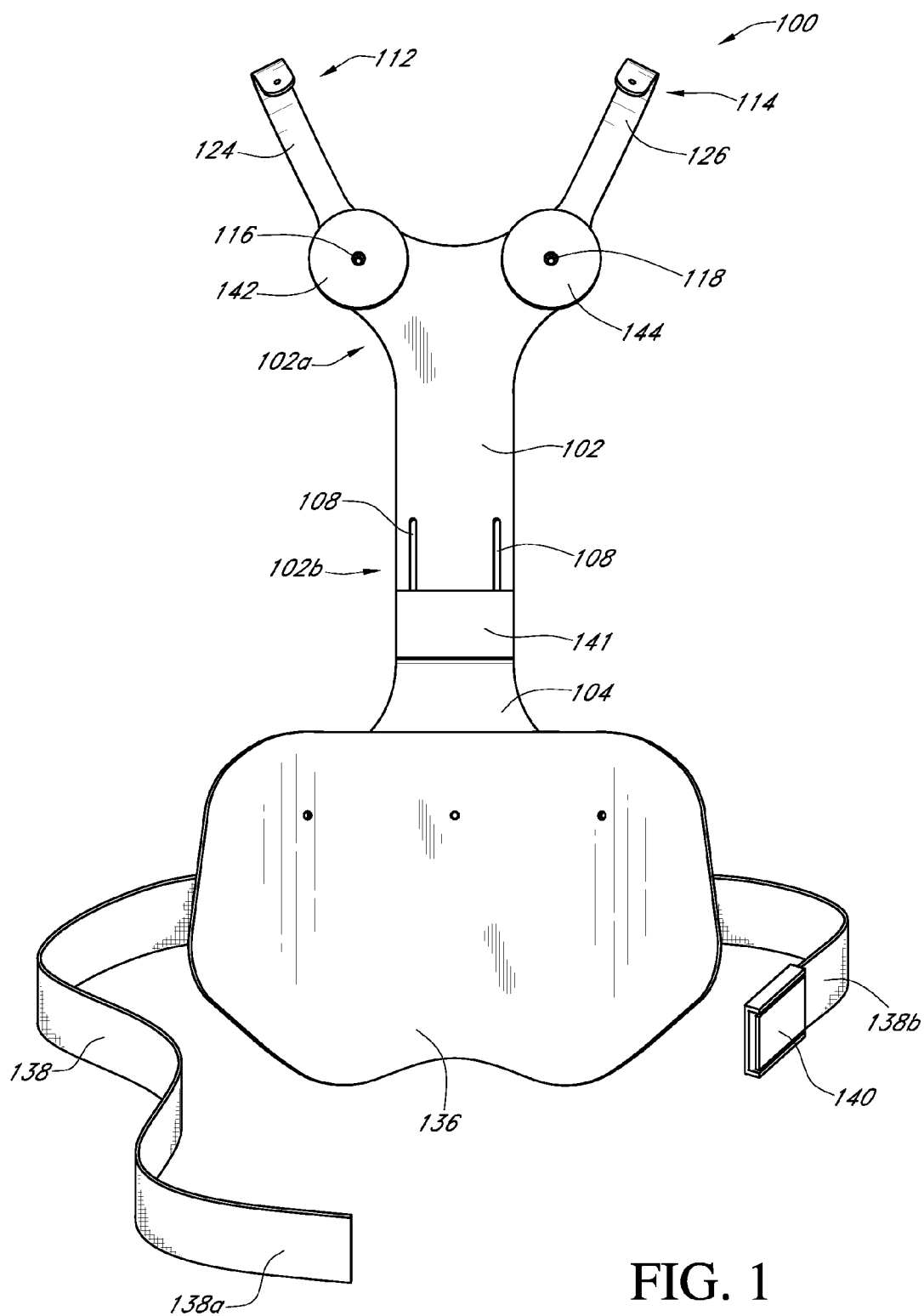
FIG. 1 illustrates a front view of a support frame for a radiation shield garment, according to an embodiment of the invention.
Figure 2:
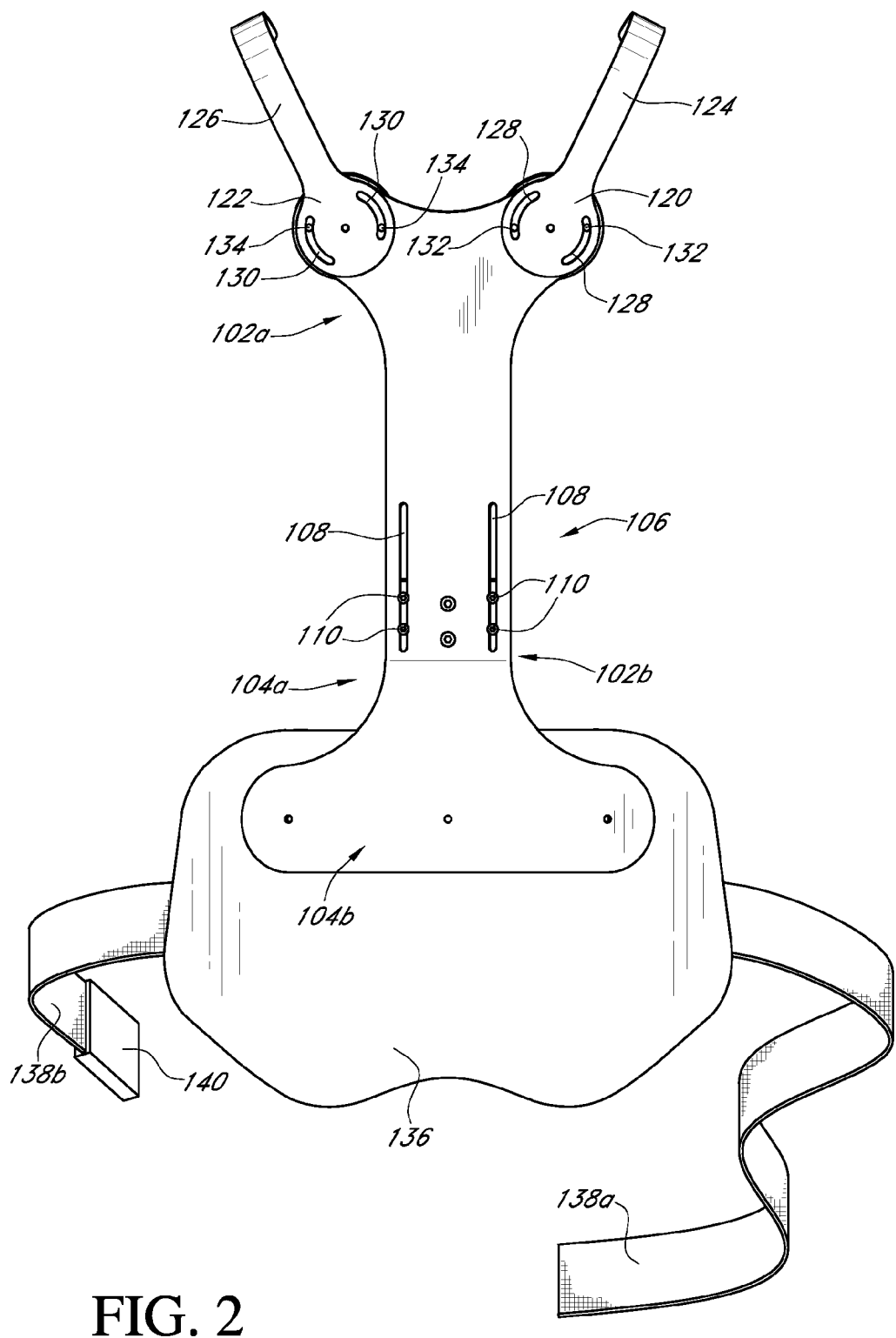
FIG. 2 illustrates a back view of the support frame for a radiation shield garment of FIG. 1.
Figure 3:
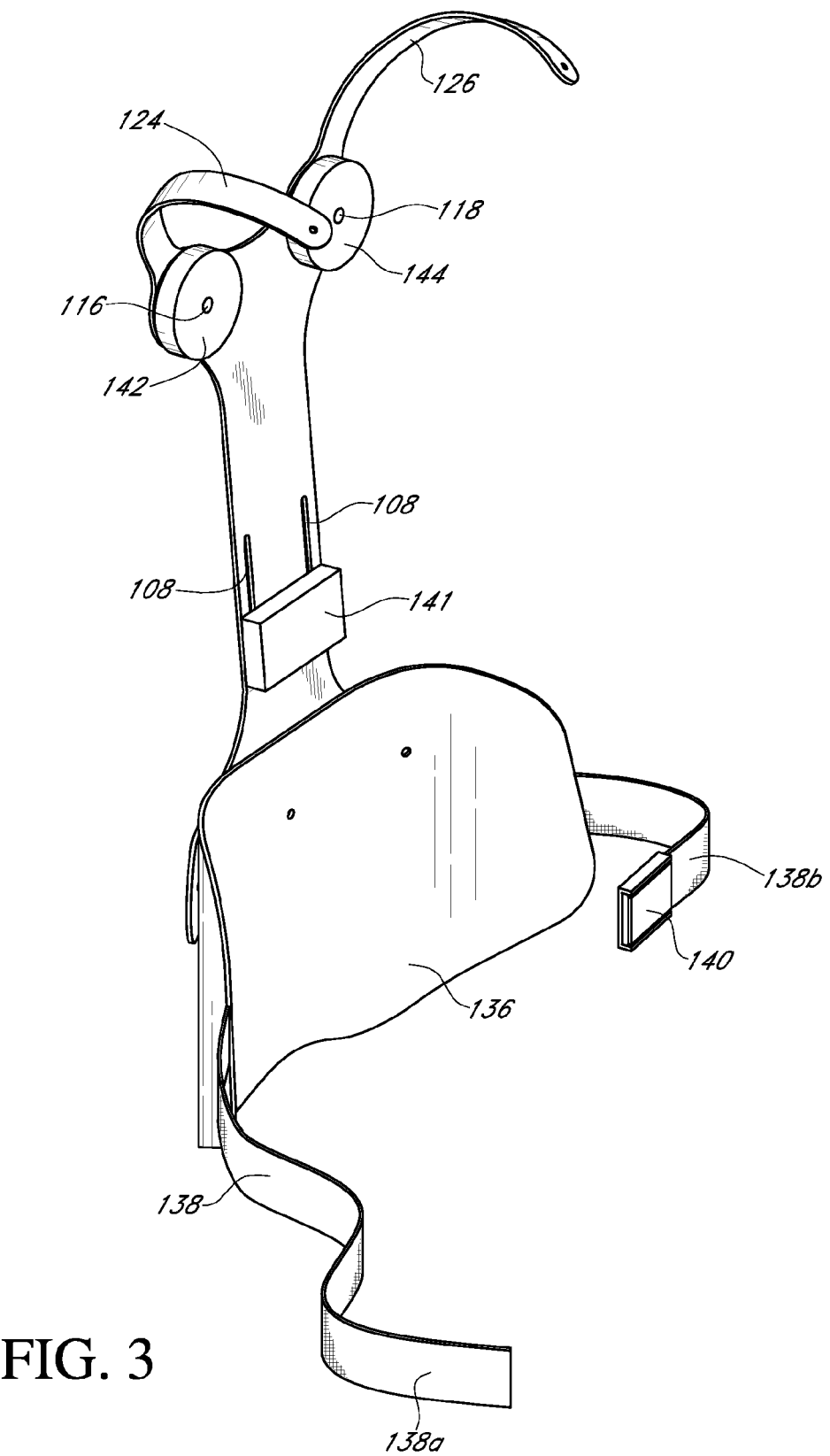
FIG. 3 illustrates a side perspective view of the support frame for a radiation shield garment of FIG. 1.

FIG. 1 illustrates a front view of a support frame for a radiation shield garment, according to an embodiment of the invention. FIG. 2 illustrates a back view of the support frame for a radiation shield garment of FIG. 1. FIG. 3 illustrates a side perspective view of the support frame for a radiation shield garment of FIG. 1. The following discussion refers interchangeably to FIGS. 1-3.

As shown, the support frame 100 includes an elongated upper vertical back member 102, having an upper top end 102a and an upper bottom end 102b, and a lower vertical back member 104, having a lower top end 104a (see FIG. 2) and a lower bottom end 104b (see FIG. 2). Upper bottom end 102b of elongated upper vertical back member 102 may be slideably attached to lower top end 104a of lower vertical back member 104 by an adjustment means 106 (see FIG. 2) and configured for placement along the back of an individual or wearer. Generally, elongated upper vertical back member 102 and lower vertical back member 104 may be formed of a substantially rigid material such as plastic, aluminum or an equivalent material. In one embodiment, the material is 5052T6 aluminum.

Adjustment means 106 may include one or more longitudinal slots 108 provided through upper bottom end 102b of elongated upper vertical back member 102 and one or more fastening members 110 extending through slots 108 providing vertical height adjustment of back panel 102 to fit different body heights. Fastening members 110 may include any type of device for connecting metal, plastic and other materials in common with support frame construction, including screws, bolts, nuts, washers, rivets, cotter pins, clevis pins, studs, threaded rods and other mechanical connectors. In an alternative embodiment, elongated upper vertical back member 102 and lower vertical back member 104 are telescoping members. According to this embodiment, the panels 102, 104 include a plurality of correlating openings on each of panels 102, 104 and one or more push pin mechanisms which lock the panels 102, 104 together at the points along the correlating openings.

In one embodiment, upper top end 102a of elongated upper vertical back member 102 may have a V-shaped configuration which approximately correlates to shoulder blades of an individual; however, other suitable shapes are within the scope of the invention. In one embodiment, lower bottom end 104b of lower vertical back member 104 may have a generally upside down T-shaped configuration which approximately correlates to the pelvic region of an individual; however, other suitable shapes are within the scope of the invention. The configuration of these components allow for maximum weight distribution associated with the support frame 100 to maximize the comfort of the wearer.

Continuing to refer to FIGS. 1-2, a pair of shoulder members 112, 114 may be connected to upper top end 102a of elongated upper vertical back member 102 at upper attachment points 116, 118, respectively. Each shoulder member 112, 114 may have a base 120, 122 (see FIG. 2) and extend into a shoulder bracket 124, 126 which project upwardly in a curved manner from bases 120, 122. Generally, shoulder brackets 124, 126 are designed to extend over the shoulders of the wearer. Similar to panels 102, 104, each shoulder member may be formed of a substantially rigid material such as plastic, aluminum or an equivalent material. Bases 120, 122 may have a generally circular configuration; however, other suitable shapes are within the scope of the invention. Bases 120, 122 approximately correlate to shoulder blades of the wearer.

In one embodiment, each base 120, 122 includes one or more circular or semi-circular slots 128, 130 and one or more fastening means 132, 134 extending through slots 128 providing angular adjustment of rigid attachment straps 124, 126 to fit different sized shoulders of wearers. Fastening means 132, 134 may include any type of device for connecting metal, plastic and other materials in common support frame construction, including screws, bolts, nuts, washers, rivets, cotter pins, clevis pins, studs, threaded rods and other mechanical connectors.

In one embodiment, a lower back support panel 136 may be fixedly coupled to upper bottom end 104a of lower vertical back member 104 and positioned to rest upon the lower back region of the wearer to improve wearer comfort. Lower back lower support member 136 may be secured to T-shaped portion of lower vertical back member 104 by a fastening mechanism including, but are not limited to, screws, bolts, nuts, washers, rivets, cotter pins, clevis pins, studs, threaded rods and other mechanical connectors. Similar to panels 102, 104, each shoulder member may be formed of a substantially rigid material such as plastic, aluminum or an equivalent material, however, the inner surface therefore may have a resilient foam material attached thereto to provide comfort to the wearer. In one embodiment, the material is polypropylene.

Lower back lower support member 136 may include a strap 138 for extending generally about the waist or hips of the wearer for securing support frame 100 to the wearer. Strap 138 may include a first end 138a and a second end 138b and be integrally formed with lower back lower padded member 136 or may be detachably secured to lower back lower padded member 136. Second end 138b may include a connector or attaching member 140 integral thereto. First end 138a of strap 138 may be adapted to pass through attaching member 140 providing adjustment to fit different body sizes. First end 138a and second end 138b may also be attached by any other suitable means, such as such as hook and loop fastener sold under the name Velcro™. A material comprising the strap 138 may be, e.g., polypropylene webbing while a material comprising the connector 140 may be, e.g., acetal.

In one embodiment, lower back lower support member 136 may have a generally rectangular configuration having a straight top edge, a generally S-shaped bottom edge in between two sloping side edges; however, other suitable shapes are within the scope of the invention. In any embodiment, support member 136 correlates in configuration to the lower back region of an individual. That is, support member 136 is approximately concave in configuration (see FIG. 3). A resilient foam material may adhere to the inner surface of support member 136 to provide additional support and comfort to the wearer.

According to embodiments of the invention, an inwardly facing center padded member 141 formed of a resilient foam material, foam/cloth combination, or any other suitable material, may be fixedly coupled to lower top end 104a of lower vertical back member 104 and positioned to rest upon the lower back area or region of the wearer to improve wearer comfort. Inwardly facing center padded member 141 may be secured to lower top end 104a by a fastening mechanism including, but not limited to, screws, bolts, nuts, washers, rivets, cotter pins, clevis pins, studs, threaded rods and other mechanical connectors. In one embodiment, the fastening mechanisms are 8/32 well nuts, 8/32 cap head screw and insulator Teflon® washer. In one embodiment, inwardly facing center padded member 141 may have a generally rectangular configuration; however, other suitable shapes are within the scope of the invention.

In one embodiment, one or more inwardly facing upper padded members 142, 144 formed of a resilient foam material, foam/cloth combination, or any other suitable material, may be fixedly coupled to bases 120, 122 of shoulder members 112, 114 and positioned to rest upon the shoulder area or region of the wearer to improve wearer comfort. The inwardly facing upper padded members 142, 144 may be secured to bases 120, 122 by a fastening mechanism including, but are not limited to, screws, bolts, nuts, washers, rivets, cotter pins, clevis pins, studs, threaded rods and other mechanical connectors. The inwardly facing upper padded members 142, 144 may have a generally circular configuration; however, other suitable shapes are within the scope of the invention.

Figure 4:
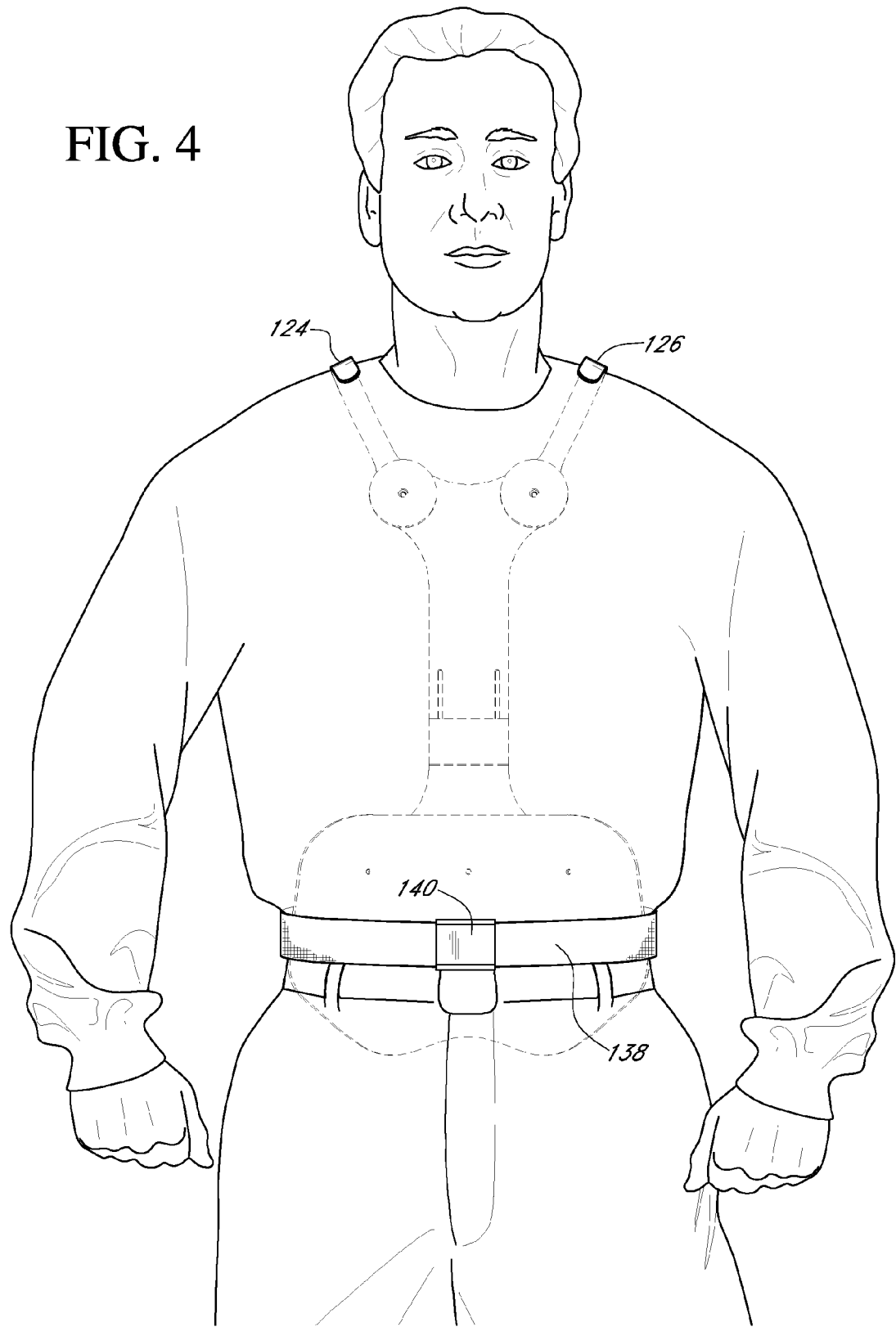
FIG. 4 illustrates a front view of the support frame for a radiation shield garment of FIG. 1 mounted on a wearer.
Figure 5:
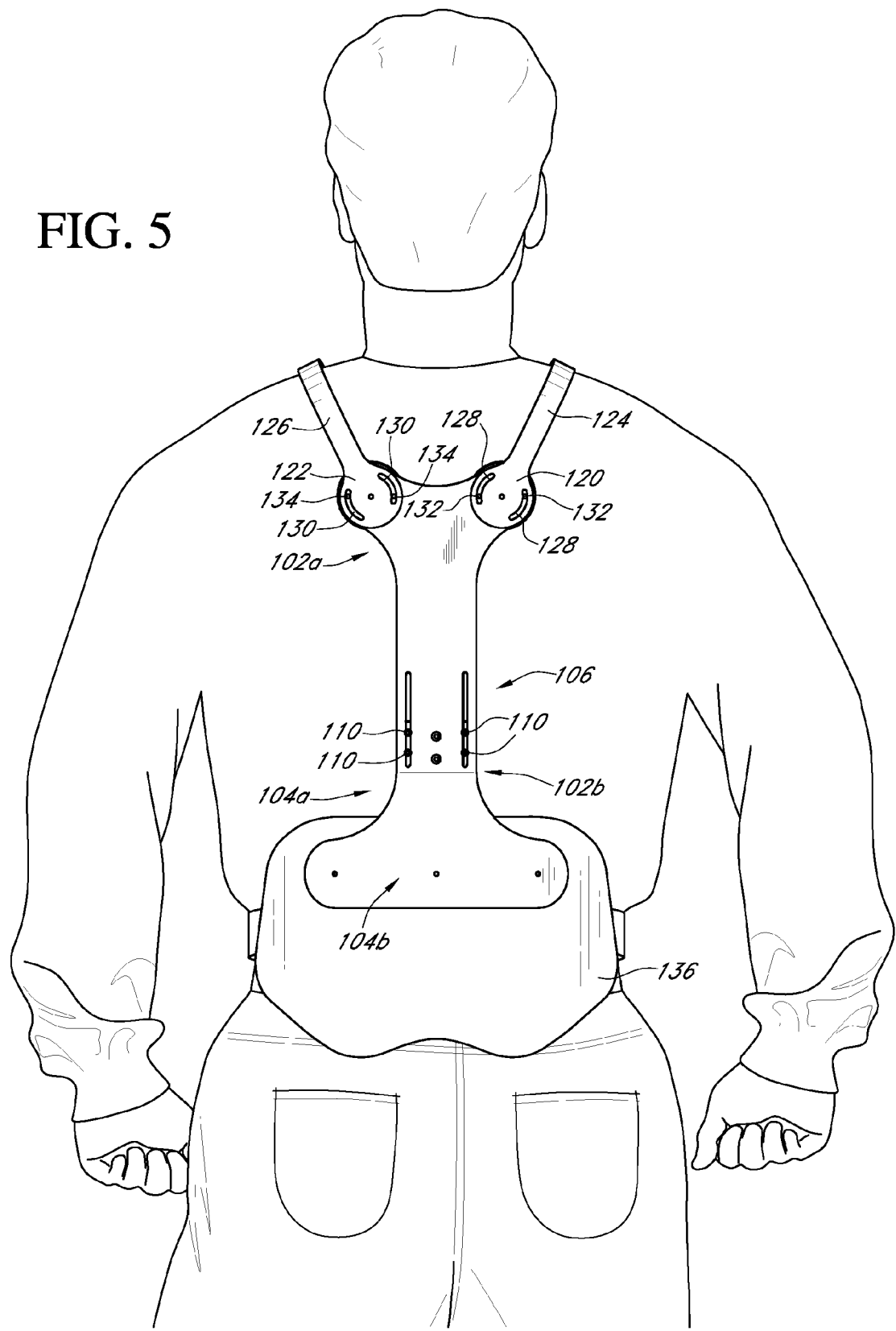
FIG. 5 illustrates a back view of the support frame for a radiation shield garment of FIG. 1 mounted on a wearer.

FIGS. 4-5 illustrate front and back views, respectively, of support frame 100 of FIG. 1 mounted on a wearer.

According to embodiments of the invention, the support frame as previously described may be used by any medical or healthcare personnel who must don a radiation shield garment on a routine basis, e.g., radiologists, ultrasound technicians and dental technicians. Instead of the radiation shield garment conventionally resting on the shoulders, the support frame according to embodiments of the invention may be positioned on the wearer with the radiation shield garment being positioned thereon. The support frame effectively redistributes the weight of the radiation shield garment by securing to the hip region of the wearer which can accommodate a larger payload (relative to the shoulders). Additionally, the shoulder members effectively lift the weight of the radiation shield garment from the shoulders of the wearer and distribute that weight along the support frame. Thus, the wearer is still protected by the radiation shield garment while realizing increased comfort from repeatedly wearing the radiation shield garment.

While certain exemplary embodiments have been described and shown in the accompanying drawings, it is to be understood that such embodiments are merely illustrative of and not restrictive on the broad invention, and that this invention is not to be limited to the specific constructions and arrangements shown and described, since various other modifications may occur to those ordinarily skilled in the art.

What is claimed is:

1. A support frame for a radiation shield garment, comprising:
   an elongated upper vertical back member, having an upper top end and an upper bottom end;
   a lower vertical back member, having a lower top end and a lower bottom end, the lower top end of the lower vertical back member slideably attached to the upper bottom end of the elongated upper vertical back member;
   a lower back support panel coupled to the lower bottom end of the lower vertical back member; and
   a pair of shoulder members attached to the upper top end of the elongated vertical back member;
   wherein the upper top end of the elongated upper vertical back member has a V-shaped configuration and the lower bottom end of the lower vertical back member has an upside down T-shaped configuration.

2. The support frame of claim 1 wherein each shoulder member comprises:
   a base; and
   a shoulder bracket projecting upwardly in a curved manner from the base for extending over shoulders of a wearer.

3. The support frame of claim 2 wherein the base includes one or more slots providing angular adjustment of the pair of shoulder members and wherein one or more fasteners extend through the one or more slots slideably attaching the each shoulder member to the upper top end of the elongated upper vertical back member.

4. The support frame of claim 2, further comprising, one or more inwardly facing upper padded members coupled to the base of the each of the pair of shoulder members and positioned to rest upon a shoulder area of the wearer.

5. The support frame of claim 1 wherein the upper bottom end of the elongated upper vertical back member includes one or more longitudinal slots; and wherein one or more fastening means extend through the elongated slots providing vertical height adjustment of the elongated upper vertical back member.

6. The support frame of claim 1 wherein the lower back support member is positioned to rest upon a lower back area of a wearer.

7. The support frame of claim 6, further comprising, a strap integrally connected to the lower back support member.

8. The support frame of claim 7 wherein the strap comprises a first end and a second end, the second end comprising an attaching means integral thereto.

9. The support frame of claim 1, further comprising, a inwardly facing center padded member attached to the upper bottom end of the lower vertical back member and positioned to rest upon a lower back area of a wearer.

10. The support frame of claim 1, wherein the elongated upper vertical back member, the lower vertical back member, and the pair of shoulder members attached to the upper top end of the elongated vertical back member are comprised of a material selected from the group consisting of aluminum and polypropylene.

11. A support frame for a radiation shield garment, comprising:
   an elongated upper vertical back member, having an upper top end and an upper bottom end, the upper top end branching into a left portion and a right portion;
   a lower vertical back member, having a lower top end and a lower bottom end, the lower top end of the lower vertical back member slideably attached to the upper bottom end of the elongated upper vertical back member;
   a lower back support member attached to the lower bottom end of the lower vertical back member; and
   a pair of shoulder members attached to the upper top end of the elongated vertical back member, each of the pair of should members comprising:
      a base; and
      a rigid attachment strap projecting upwardly in a curved manner from the base for extending over shoulders of a wearer;
   wherein the upper top end of the elongated upper vertical back member has a V-shaped configuration and the lower bottom end of the lower vertical back member has an upside down T-shaped configuration.

12. The support frame of claim 11 wherein the base includes one or more slots providing angular adjustment of the pair of shoulder members and wherein one or more fasteners extend through the one or more slots slideably attaching the each shoulder member to the upper top end of the elongated upper vertical back member.

13. The support frame of claim 11 wherein the upper bottom end of the elongated vertical back member includes one or more longitudinal slots; and wherein one or more fastening means extend through the elongated slots providing vertical height adjustment of the elongated upper vertical back member.

14. The support frame of claim 11, further comprising a strap integrally connected to the lower back lower padded member.

15. The support frame of claim 14, wherein the strap comprises a first end and a second end, the second end comprising an attaching means integral thereto.

16. The support frame of claim 11, further comprising an inwardly facing center padded member attached the upper bottom end of the lower vertical back member and positioned to rest upon a lower back area of the wearer.

17. The support frame of claim 11, wherein the elongated upper vertical back member, the lower vertical back member, and the pair of shoulder members attached to the upper top end of the elongated vertical back member are comprised of aluminum.

18. A support frame for a radiation shield garment, comprising:
   an elongated upper vertical back member, having an upper top end and an upper bottom end, the upper top end having a V-shaped configuration;
   a lower vertical back member, having a lower top end and a lower bottom end, the lower top end of the lower vertical back member slideably coupled to the upper bottom end of the elongated upper vertical back member;
   a lower back support member attached to the lower bottom end of the lower vertical back member, the lower bottom end having an upside down T-shaped configuration;
   an inwardly facing center padded member attached to the upper bottom end of the lower vertical back member and positioned to rest upon the lower back of the wearer;
   a pair of shoulder members attached to the upper top end of the elongated vertical back member, each of the pair of should members comprising:
      a base;
      a shoulder bracket projecting upwardly in a curved manner from the base for extending over shoulders of a wearer; and
      an inwardly facing upper padded member coupled to the base the each of the pair of shoulder members and positioned to rest upon a shoulder area of the wearer.

* * * * *